United States Patent [19]

Müller et al.

[11] Patent Number: 4,855,484

[45] Date of Patent: Aug. 8, 1989

[54] PROCESS FOR THE PREPARATION OF 4-HYDROXYPHENYL 4-HYDROXYBENZOATE AND THE USE THEREOF

[75] Inventors: Hanns P. Müller, Odenthal; Roland Gipp, Cologne, both of Fed. Rep. of Germany

[73] Assignee: Bayer Aktiengesellschaft, Leverkusen, Fed. Rep. of Germany

[21] Appl. No.: 64,679

[22] Filed: Jun. 22, 1987

[30] Foreign Application Priority Data

Jul. 5, 1986 [DE] Fed. Rep. of Germany ....... 3622611

[51] Int. Cl.$^4$ ............................................. C07C 69/88
[52] U.S. Cl. ..................................................... 560/72
[58] Field of Search .......................................... 570/72

[56] References Cited

U.S. PATENT DOCUMENTS 2,811,461  10/1957  Meyer et al. ......................... 560/72
4,038,250  7/1977  Lind ..................................... 560/72

FOREIGN PATENT DOCUMENTS 0139252   5/1985  European Pat. Off. .
60-34932   2/1985  Japan .
60-237048  11/1985  Japan .

OTHER PUBLICATIONS

CA77(22):140738m 1972.
CA97(8):56436s 1982.
CA97(4):24503v 1982.
CA100(16):121877h 1984.

*Primary Examiner*—Paul J. Killos
*Attorney, Agent, or Firm*—Connolly & Hutz

[57] ABSTRACT

A process for the preparation of 4-hydroxyphenyl 4-hydroxy-benzoate by esterification of hydroquinone and p-hydroxybenzoic acid is described, wherein an esterification catalyst is used and wherein the reaction is carried out in a reaction medium in which the reactants are substantially dispersed. The use of the compound, accessible by the above process in high yield and good industrial purity, for the preparation of linear polycarbonates or copolycarbonates is furthermore claimed.

6 Claims, No Drawings

PROCESS FOR THE PREPARATION OF 4-HYDROXYPHENYL 4-HYDROXYBENZOATE AND THE USE THEREOF

A process for the preparation of 4-hydroxyphenyl 4-hydroxy-benzoate by esterification of hydroquinone and p-hydroxybenzoic acid is described, wherein an esterification catalyst is used and wherein the reaction is carried out in a reaction medium in which the reactants are substantially dispersed. The use of the compound, accessible by the above process in high yield and good industrial purity, for the preparation of linear polycarbonates or copolycarbonates is furthermore claimed.

Building blocks in syntheses for the construction of novel polymers which contain LC (liquid crystal) building blocks in the main and/or side chain have been increasing in importance for some time.

In Eur. Polym. J. 20 (3), 225 (1984), W. R. Krigbaum et al. describe a study on polymers based on 4-hydroxyphenyl 4-hydroxybenzoate. In this work, the authors show that the use of pure building blocks in the construction of aromatic polyesters very essentially influence the property profile of the resulting aromatic polyesters.

J. Jackson Jr., in his publication in Brit. Polym. J. 12 (1980), 154, also comes to the conclusion that the best properties of aromatic polyesters are obtained when only symmetrically oriented aromatic rings are used for the construction of the polyesters.

However, the synthesis of pure 4-hydroxyphenyl 4-hydroxy-benzoate (I)

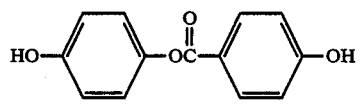

as a building block for polymers has hitherto not succeeded on an industrial scale. Thus, Krigbaum, in the abovementioned work, describes only a complicated synthesis using protecting groups.

The present invention relates to a process for the preparation of 4-hydroxyphenyl 4-hydroxybenzoate (I) by reacting p-hydroxybenzoic acid and hydroquinone in approximately equivalent molar ratios, wherein an esterification catalyst is used and wherein the reaction is carried out in a reaction medium in which the reactants are substantially dispersed. In a preferred embodiment the reactants are sparingly soluble in the reaction medium and the formed 4-hydroxyphenyl-4-hydroxybenzoate is even more sparingly soluble. A preferred catalyst is the combination of sulphuric acid and boric acid. Especially preferred catalysts are sulfonic acids, especially aromatic sulfonic acids e.g. p-toluene sulfonic acid.

The invention also relates to the use of 4-hydroxyphenyl-4-hydroxybenzoate (I) as a polymer-building block for the construction of linear, aromatic polycarbonates by the condensation process. Preferred here is the use of 4-hydroxyphenyl 4-hydroxybenzoate which is prepared by the process according to the invention.

To carry out the process according to a preferred embodiment the catalysts e.g. 0.01 to 3, preferably 0.1 to 1.5% by weight of boric acid and 0.01 to 3, preferably 0.1 to 1.5% by weight of concentrated sulphuric acid are added to the starting components 4-hydroxybenzoic acid and hydroquinone in an inert solvent, preferably an aromatic hydrocarbon, for example toluene or xylene, and the mixture is esterified under reflux and with removal of the water of condensation, for example through a water separator). Preferably used is a boric acid/sulphuric acid mixture containing 25 to 70 parts by weight of boric acid and 75 to 30 parts by weight of sulphuric acid, in particular about 40 to 60 parts by weight of boric acid and 60 to 40 parts by weight of concentrated sulphuric acid. The esterification reaction in the heterogeneous mixture (when using xylene as solvent) is completely after 3.5 to 4 hours. In the case of lower-boiling solvents such as toluene, the esterification time is extended until virtually complete water separation has occurred. The batch is allowed to cool, and the well-crystallized crude product is rapidly filtered off under suction, and washed with an inert solvent, preferably xylene or toluene, then with dilute sodium hydrogen carbonate solution and subsequently with water. After drying, 4-hydroxyphenyl 4-hydroxy-benzoate is obtained in a yield of 98.5% of theory; melting point 242°-245° C. (when using xylene as solvent). In another preferred embodiment the combination sulfuric acid/boric acid is replaced by p-toluene sulfonic acid.

4-Hydroxy-phenyl 4-hydroxybenzoate can be used for the preparation of polyesters having particular properties which are based on the liquid-crystalline character of the structural components. According to the invention, it is used for the construction of linear polycarbonate polymers which have the typical properties of polymers containing liquid-crystalline building blocks. These are, in particular, increased strength values in approximately the orientation direction of the liquid-crystalline building blocks within the polymer.

The use of 4-hydroxy-phenyl 4-hydroxybenzoate (I) for the preparation of three-dimensionally crosslinked polymers is the subject of a German Patent Application P 3 622 613 filed simultaneously. The compound (I), accessible according to the invention, also serves as an intermediate for the preparation of starting materials having a liquid-crystalline character, for example bis-epoxide, see German Patent Application P 3 622 610 filed simultaneously.

EXAMPLE 1

Preparation of 4-hydroxy-phenyl 4-hydroxy-benzoate (I) Batch
 414 g (3 mol) of 4-hydroxy-benzoic acid
 330 g (3 mol) of hydroquinone
 1,800 ml (about 1.56 kg) of xylene
 6 g of boric acid
 4.5 ml (about 8.2 g) of concentrated sulfuric acid A mixture of the reaction components is heated to the reflux temperature (bath temperature 170°-175° C.) with vigorous stirring in a 3 liter sulphonation beaker which is equipped with a flat-flange cover, internal thermometer, V$_2$A steel stirrer and—via a water separator—a reflux condenser. A clear solution is not observed at any point during the reaction. After stirring for about 3.5 hours at the reflux temperature, the separation of the water produced by the reaction (about 55 to 56 ml; theoretically 54 ml) is complete. The mixture is stirred for a further 0.5 hours at the reflux temperature and then allowed to cool to room temperature—if possible with further stirring. The crude product, subsequently filtered off rapidly under suction, is washed with xylene and dried at room temperature under reduced pressure.

The powdered material is first washed thoroughly with 3% strength sodium hydrogen carbonate solution and then with water, and dried at room temperature under reduced pressure.

Yield: 680 g (98.5% of theory)
Melting point: 242°–245° C.

In order to remove sparingly soluble to insoluble byproducts (obviously mainly linear oligoesters), I is extracted to exhaustion from the crude product with hot acetone, I is precipitated from the extraction mixture, cooled to room temperature, by adding ice water with stirring, and is rapidly filtered off under suction and dried over silica gel at room temperature and under reduced pressure.

Yield: 563 g (81.6% of theory).

Recrystallization from glycol monomethyl ether acetate[1]) and drying as above produce 492 g (71.4%)[2]) of I of melting point 241°–243° C. of adequate purity for further reactions.

[1])If necessary with addition of activated charcoal.
[2])If the mother liquor from the recrystallization of the product of previous batch is used in place of glycol monomethyl ether acetate, I of the same purity is obtained in a yield of about 102% of theory, i.e. the overall yield from both batches is then almost 87% of theory.

EXAMPLE 2

Preparation of 4-hydroxyl-phenyl 4-hydroxy-benzoate

Batch
414 g (3 mol) of 4-hydroxy-benzoic acid
330 g (3 mol) of hydroquinone
2500 ml (about 2.17 kg) of xylene
10 g of p-toluene-sulfonic acid.

The reaction is carried out according to Example 1.
Yield: 640 g (92.7% of theory)
Melting point: 242°–245° C.).

The product does not contain oligoesters and is completely soluble in acetone.

We claim:

1. Process for the preparation of 4-hydroxyphenyl 4-hydroxybenzoate by reacting p-hydroxybenzoic acid and hydroquinone in approximately equivalent molar ratios wherein an esterification catalyst is used and wherein the reaction is carried out in a reaction medium in which the reactants are substantially dispersed.

2. Process according to claim 1, characterized in that 0.01–3% by weight of boric acid and 0.01–3% by weight of concentrated sulphuric acid are used as catalysts, relative to the solids content of the starting materials.

3. Process according to claim 1, characterized in that boric acid/sulfuric acid mixtures containing 25–70 parts by weight of boric acid and 75–30 parts by weight of sulfuric acid are used as catalysts.

4. Process according to claim 1, characterized in that sulfonic acid is used as catalyst.

5. Process according to claim 1, characterized in that p-toluene sulfonic acid is used as catalyst.

6. Process according to claim 1, characterized in that the inert solvents used are aromatic hydrocarbons and the esterification reaction is carried out under reflux with water separation.

* * * * *